United States Patent
Dunlap et al.

(10) Patent No.: US 7,666,616 B2
(45) Date of Patent: Feb. 23, 2010

(54) NUCLEIC ACID SEQUENCES ENCODING LUCIFERASE FOR EXPRESSION IN FILAMENTOUS FUNGI

(75) Inventors: Jay C. Dunlap, Thetford, VT (US); Jennifer Loros, Thetford, VT (US); Arun Mehra, Hanover, NH (US); Van D. Gooch, Morris, MN (US)

(73) Assignees: Trustees of Dartmouth College, Hanover, NH (US); Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 11/576,168

(22) PCT Filed: Sep. 30, 2005

(86) PCT No.: PCT/US2005/035325
§ 371 (c)(1),
(2), (4) Date: Apr. 3, 2007

(87) PCT Pub. No.: WO2006/049777
PCT Pub. Date: May 11, 2006

(65) Prior Publication Data
US 2008/0096279 A1 Apr. 24, 2008

Related U.S. Application Data

(60) Provisional application No. 60/614,874, filed on Sep. 30, 2004.

(51) Int. Cl.
*C12Q 1/66* (2006.01)
*C12N 9/02* (2006.01)
*C12N 15/74* (2006.01)
*C12P 21/06* (2006.01)
*C12N 15/00* (2006.01)
*C12N 1/20* (2006.01)
*C07H 21/04* (2006.01)

(52) U.S. Cl. ............... 435/8; 435/189; 435/471; 435/69.1; 435/91.1; 435/320.1; 435/252.3; 435/254.11; 435/810; 536/23.2

(58) Field of Classification Search ............. None
See application file for complete search history.

(56) References Cited

U.S. PATENT DOCUMENTS

| | | | |
|---|---|---|---|
| 5,670,356 A * | 9/1997 | Sherf et al. ............ 435/189 |
| 5,795,737 A | 8/1998 | Seed et al. | |
| 5,811,238 A | 9/1998 | Stemmer et al. | |
| 5,837,458 A | 11/1998 | Minshull et al. | |
| 2004/0142356 A1 * | 7/2004 | Patterson et al. ............ 435/6 |

OTHER PUBLICATIONS

Hoover et al., DNAWorks: an automated method for designing oligonucleotides for PCR-based gene synthesis. Nuc. Acids Res., 2002, vol. 30 (1): e43 pp. 1-8.*
Gustaffson et al., Codon bias and heterologous protein expression. Trends in Biotechnol., Jul. 2004, vol. 22 (7): 346-353.*
Branchini et al., "Site-Directed Mutagenesis of Histidine 245 in Firefly Luciferase: A Proposed Model of the Active Site", Biochemistry 1998 37:15311-15319.
Franklin et al., "Development of a GFP reporter gene for *Chlamydomonas reinhardtii* chloroplast", The Plant Journal 2002 30(6):733-744.
Budisa et al., "Toward the experimental codon reassignment in vivo:protein building with an expanded amino acid repertoire", FASEB J. 1999 13:41-51.
Campbell et al,, "Codon Usage in Higher Plants, Green Algae and Cyanobacteria", Plant Physiol. 1990 92:1-11.
Fourrier et al., "Simple, powerful promotoer and enhancer analysis with the MightLight System", inNovations, Mar. 2003 16:13-16.
Kajiyama et al., "Enhancement of Thermostability of Firefly Luciferase from *Luciola lateralis* by a Single Amino Acid Substitution", Biosci. Biotech. Biochem. 1994 58(6):1170-1171.
Marin et al., "Variation in G+C-content and codon choice:differences among synonymous codon groups in vertebrate genes", Nucleic Acids Research 1989 17(15):6181-6189.
Satya et al., "A Pattern Matching Algorithm for Codon Optimization and CpG Motif-Engineering in DNA Expression Vectors", IEEE 2003.
Sung et al., "The N-Terminal Amino Acid Sequences of the Firefly Luciferase Are Important for the Stability of the Enzyme", Photochemistry and Photobiology 1998 68(5):749-753.
White et al., "Improved thermostability of the North American firefly luciferase:saturation mutagenesis at position 354", Biochem J. 1996 319:343-350.

* cited by examiner

*Primary Examiner*—Ganapathirama Raghu
(74) *Attorney, Agent, or Firm*—Licata & Tyrrell P.C.

(57) ABSTRACT

The present invention relates to genetic reporters. Specifically, the present invention is directed to a modified gene encoding a luciferase for high level expression in an organism with a bias for cytosine (C) or guanine (G) in the third position of the codon.

7 Claims, 4 Drawing Sheets

```
NATIVE    ATGGAAGAGACGCCAAAAACATAAAGAAAGGCCCGGCGCCATTCTATCCTCTAGAGGATGGA  60
VARIANT   ATGGAAGAGACGCCAAGAAGAAGAAGCCCGCCCCGCCCCCTTCTACCCCTCGAGGACGGC    60
          ************  ** ** ** ** **** ** ** ** **** **** ****** **

NATIVE    ACCGCTGGAGAGCAACTGCATAAGGCTATGAAGAGATACGCCCTGGTTCCTGGAACAATT  120
VARIANT   ACCGCCGGCGAGCAGCTGCACAAGGCCATGAAGCGCTACGCCCTCGTCCCCGGCACCATC  120
          ***** ** ***** ***** ***** ***** * ******** ** ** ** ** **

NATIVE    GCTTTTACAGATGCACATATCGAGGTGAACATCACGTACGCGGAATACTTCGAAATGTCC  180
VARIANT   GCCTTCACCGACGCGCACATCGAGGTCAACATCACCTACGCCGAGTACTTCGAGATGTCC  180
          ** ** ** ** ** ****** **** ********  ***** ** ******* *****

NATIVE    GTTCGGTTGGCAGAAGCTATGAAACGATATGGGCTGAATACAAATCACAGAATCGTCGTA  240
VARIANT   GTCCGCCTCGCCGAGGCCATGAAGCGCTACGGCCTCAACACCAACCACCGCATCGTCGTC  240
          **  **  * ** ** ** ***** * ** ** ** ** ** ** ** * ********

NATIVE    TGCAGTGAAAACTCTCTTCAATTCTTTATGCCGGTTGTTGGGCGGTTATTTATCGGAGTT  300
VARIANT   TGCTCCGAGAACTCCCTGCAGTTCTTCATGCCCGTCCTCGGCGCCCTCTTCATCGGCGTC  300
          *** * ** ***** ** ** ***** ***** **  * ***  * ** ***** **

NATIVE    GCAGTTGCGCCCCGCGAACGACATTTATAATGAACGTGAATTGCTCAACAGTATGAACATT  360
VARIANT   GCCGTCGCGCCCCGCGCCAACGACATCTACAACGAGCGCGAGCTCCTCAACTCCATGAACATC  360
          ** ** ********  * *******  * ** ** ** ** ** ****   *********

NATIVE    TCGCAGCCTACCGGTAGTGTTTGTTTCCAAAAAGGGGTTGCAAAAATTTTGAACGTGCAA  420
VARIANT   TCCCAGCCCACCGGCTCCGTCGTCTTCTCCCAAGAGATCCTCAAGATCCTCAACGTCCAG  420
          ** ***** ***** * *** * *** **** ** ** ** **** * ** ****** **

NATIVE    AAAAAATTACCAATAATCCAGAAAATTATTATCATGGATTCTAAAACGGATTACCAGGGA  480
VARIANT   AAGAAGCTCCCCATCATCCAGAAGATCATCATGGACTCCAAGACTCCAAGAACGACGAGGC  480
          ** ** ** ** ** ********* * ***** ** ***** *    ** ** ** **

NATIVE    TTTCAGTCGATGTACACGTTCGTCACATCTCATCCTCACCTCCCCGGTTTTAATGAATACGAT  540
VARIANT   TTCCAGTCCATGTACACCTTCGTCACCTCCCCCCCTCCCCGGCTTCAACGAGTACGAC    540
          ** ***** ******** ********  * ** ** *** ** ** ** ** ****
```

FIG. 2A

```
NATIVE   TTTGTACCAGAGTCCTTTGATCGTGACAAATTGCACTGATAATGAATTCCTCTGA 600
VARIANT  TTCGTCCCGAGTCCTCGACCGCGACAAGACCATCGCCCTCATCATGAACTCCTCCGGC 600
         **  * ***** **** ** **    **  *  ** **  *  ***** * ** *

NATIVE   TCTACTGGGTTACCTAAGGGTGTGGCCCCTTCCGCATAGAACTGCCTGCGTCAGATTCTCG 660
VARIANT  TCCACCGGCCTCCCCAAGGGCGTCGCGCCCTCCCGCACCGAACCGCCGCTGCGTCCGCTCTCC 660
         **  * ** ** ** ***** **  ** *** ****   * ** ** ** * * *  *

NATIVE   CATGCCAGAGATCCTATTTTTGGCAATCAAATCATTCCGGATACTGCGATTTTAAGTGTT 720
VARIANT  CACGCCCGCGACCCCATCTTCGGCAACCAGATCATCCCCGACACCGCCATCCTCTCCGTC 720
         ** ***  * * ** ** ** *****  * ***** * ** ** ** **   *  *

NATIVE   GTTCCATTCCATCACGGTTTTGGAATGTTTACTACACTCGGATATATTTGATATGTGGATTT 780
VARIANT  GTCCCCTTCCACCACCGGCTTCGGCATGTTCACCACCCTCGGCTACCTCATCATGCGGCTTC 780
         **  * ***** **  ** ** ** ***** ** ** ***** *  * **  *  **

NATIVE   CGAGTCGTCTTAATGTATAGATTTGAAGAAGAGCTGTTTTACGATCCCTTCAGGATTAC 840
VARIANT  CGCGTCGTCCTCATGTACCGCTTCGAGGAGGAGCTCTTCCTCCGCTCCCCTCCAGACTAC 840
         ** ******  * ****   * * ** ** ****  **  * **  ** *** * ***

NATIVE   AAAATTCAAAGTGCGTTGCTAGTACCAACCCTATTTTCATTCTTCGCCAAAAGCACTCTG 900
VARIANT  AAGATCCAGTCCGCCCTCCTCGTCCCCACCCTCTTCTCCTTCCTCGCCAAGTCCCACCCTC 900
         **  * **    **  *  ** ** *****  *   *  **  ****** *  **  **

NATIVE   ATTGACAAAATACGATTTATCTAATTTACACGAAATTGCTTCTGGGGGCGCACCCTCTTTCG 960
VARIANT  ATCGACAAGTACGACCCCCACCTCCACCTCCACGAGATCGCCCTCGCGGCCGGCCCCTCTCC 960
         ** *****  **** * **  * * *  ** ** ** ** * *   ** *  **   **

NATIVE   AAAGAAGTCGGGGAAGCGGTTGCAAAACGCTTCCATCTTCCAGGATACGACAAGGATAT 1020
VARIANT  AAGGAGGTCGGCGAGGTCGGCCTCGCCAAGCGCTTCGCCCATCCGCGCGATCCGCAGGCTAC 1020
         **  * ***** ** ** *** ** ** **  ** ***  ** ***** ** **  **

NATIVE   GGGCTCACTGAGACTACATCAGCTATTCTGATTACACCGCCATCTCCGCCATCCGCCGGC 1080
VARIANT  GGCCTCACCGAGACCGAGACCCGCCATCAGCTCCGCCATCCGCCGACGAGCGACGACGAC 1080
         ** *****  ****   *     *  ** *     *   *   **    *   *
```

FIG. 2B

| | | |
|---|---|---|
| NATIVE | GCGGTCGGTAAAGTTGTTCTTCCATTTTTTGAAGCGAAGGTTGTGGATCTCGGATACCGGGAAA | 1140 |
| VARIANT | GCCGTCGGCAAGGTCGTCGTCCCCTTCTTCGAGGCCAAGGTCGTCGACCTCGACACCGGCAAG | 1140 |
| | ** ***** ** ** ** ****** ***** ** ****** ** ** ***** ** | |
| NATIVE | ACGCTGGGCGTTAATCAGAGAGGCGAATTATGTGTCAGAGGACCTATGATTATGTCCGGT | 1200 |
| VARIANT | ACCCTCGGCGTCAACCAGCGCGGCGAGCTCTGCGTCGCGGCCCCCATGATCATGTCCGGC | 1200 |
| | ** ** ***** ** ** ** ** ** ** *** ** ****** ** ****** | |
| NATIVE | TATGTAAAACAATCCGGACCAACGCCCTTGATTGACAAGGATGGATGGCTACATTCT | 1260 |
| VARIANT | TACGTCAACAACCCCGAGGCCACCACGCCCTCATCGACAAGGACGGCTGGCTCCACTCC | 1260 |
| | ** ** ** ** ** ** ** ** ****** ***** *** ** ** | |
| NATIVE | GGAGACATAGCTTACTGGGACGAAGACACACTTCTTCATAGTTGACCGCTTGAAGTCT | 1320 |
| VARIANT | GGCGACATCGCCTACTGGGACGAGGACGAGCACTTCTTCATCGTCGACCGCCTCAAGTCC | 1320 |
| | ** ***** ** ************ ** ** ****** ** ******** ** *** | |
| NATIVE | TTAATTAAATACAAAGGATATATCAGGTTGGCCCCCCGCTGAATTGGAATCGATATTGTTACAA | 1380 |
| VARIANT | CTCATCAAGTACAAGGGCTACATCCAGGTCGCCCCCGCCGAATCGAGTCCGAGTCCTCCTCCAG | 1380 |
| | ** ** ** ***** ** ** ****** *** ***** *** ** *** *** ** | |
| NATIVE | CACCCCAACATCTTCGACGTCTTGTTTGGCAGGTCTTCCCGACGATGACGCCGGTGAACTT | 1440 |
| VARIANT | CACCCCAACATCTTCGACGTCTCGCCGGCCAGGTCCTCGCCCGACGACGACGCCGGAGCTC | 1440 |
| | **************** *** ***** ** ** ** ****** ** ****** | |
| NATIVE | CCCGCCCGCCGTGTTGTTTGGGAGCACGGAAAAGACGATGACGGAAAAAGAGATCGTGGAT | 1500 |
| VARIANT | CCCGCCGCCCGTGTCGTCCTCGACGTCCTCGAGCACGACGAAGACCATGACCGAGAGGAGATCGTCGAC | 1500 |
| | ****** ** ***** ** ** ** ** ****** ***** ** ** ** | |
| NATIVE | TACGTCGCCAGTCAAGTAACAACCGCGAAAAAGTTGCGCGGAGGAGTTGTGTTTCGTGGAC | 1560 |
| VARIANT | TACGTCGCCTCCCAGTCACCACCGCCAAGAAGCTCCGCGCGCTCGTCGTCTTCGTCGAC | 1560 |
| | ********* ***** ** ***** ** ** ** **** ** ** ***** *** | |
| NATIVE | GAAGTACCGAAAGGTCTTACCGGAAAAACTCGACGGCAAGACGCCGAGAGATCCTCATA | 1620 |
| VARIANT | GAGGTCCCCAAGGGCCCTCACCGGCCCCCAAGACGCTCGACGCCGCAAGATCCGAGATCCTCATC | 1620 |
| | ** ** ** ** *** ****** ***** ** ****** ** | |
| NATIVE | AAGGCCAAGAAGGGCGGAAAGTCCAAATTGTAA 1653 (SEQ ID NO:2) | |
| VARIANT | AAGGCCAAGAAGGGCGGCGGCCAAGTCCAAGCTCTGA 1653 (SEQ ID NO:1) | |

SEQUENCE LISTING

```
<160> NUMBER OF SEQ ID NOS: 5

<210> SEQ ID NO 1
<211> LENGTH: 1653
<212> TYPE: DNA
<213> ORGANISM: Artificial Sequence
<220> FEATURE:
<223> OTHER INFORMATION: Synthetic luciferase nucleic acid

<400> SEQUENCE: 1
atggaggacg ccaagaacat caagaagggc cccgccccct tctacccct cgaggacggc      60 accgccggcg agcagctcca caaggccatg aagcgctacg ccctcgtccc cggcaccatc     120
gccttcaccg acgcccacat cgaggtcaac atcacctacg ccgagtactt cgagatgtcc     180
gtccgcctcg ccgaggccat gaagcgctac ggcctcaaca ccaaccaccg catcgtcgtc     240
tgctccgaga actccctcca gttcttcatg cccgtcctcg gcgccctctt catcggcgtc     300
gccgtcgccc ccgccaacga catctacaac gagcgcgagc tcctcaactc catgaacatc     360
tcccagccca ccgtcgtctt cgtctccaag aagggcctcc agaagatcct caacgtccag     420
aagaagctcc ccatcatcca gaagatcatc atcatggact ccaagaccga ctaccagggc     480
ttccagtcca tgtacacctt cgtcacctcc cacctccccc ccggcttcaa cgagtacgac     540
```

```
ttcgtccccg agtccttcga ccgcgacaag accatcgccc tcatcatgaa ctcctccggc    600
tccaccggcc tccccaaggg cgtcgcctc ccccaccgca ccgcctgcgt ccgcttctcc    660
cacgcccgcg accccatctt cggcaaccag atcatccccg acaccgccat cctctccgtc    720
gtccccttcc accacggctt cggcatgttc accaccctcg ctacctcat ctgcggcttc    780
cgcgtcgtcc tcatgtaccg cttcgaggag gagctcttcc tccgctccct ccaggactac    840
aagatccagt ccgccctcct cgtccccacc ctcttctcct tcttcgccaa gtccacccct    900
atcgacaagt acgacctctc caacctccac gagatcgcct ccggcggcgc ccccctctcc    960
aaggaggtcg gcgaggccgt cgccaagcgc ttccacctcc ccggcatccg ccagggctac   1020
ggcctcaccg agaccacctc cgccatcctc atcacccccg agggcgacga caagcccggc   1080
gccgtcggca aggtcgtccc cttcttcgag gccaaggtcg tcgacctcga caccggcaag   1140
accctcggcg tcaaccagcg cggcgagctc tgcgtccgcg gccccatgat catgtccggc   1200
tacgtcaaca cccccgaggc caccaacgcc ctcatcgaca aggacggctg gctccactcc   1260
ggcgacatcg cctactggga cgaggacgag cacttcttca tcgtcgaccg cctcaagtcc   1320
ctcatcaagt acaagggcta ccaggtcgcc ccgccgagc tcgagtccat cctcctccag   1380
caccccaaca tcttcgacgc cggcgtcgcc ggcctccccg acgacgacgc cggcgagctc   1440
cccgccgccg tcgtcgtcct cgagcacggc aagaccatga ccgagaagga gatcgtcgac   1500
tacgtcgcct cccaggtcac caccgccaag aagctccgcg gcggcgtcgt cttcgtcgac   1560
gaggtccccca agggcctcac cggcaagctc gacgcccgca agatccgcga gatcctcatc   1620
aaggccaaga agggcggcaa gtccaagctc tga                                1653

<210> SEQ ID NO 2
<211> LENGTH: 1653
<212> TYPE: DNA
<213> ORGANISM: Photinus pyralis

<400> SEQUENCE: 2
atggaagacg ccaaaaacat aaagaaaggc ccggcgccat tctatcctct agaggatgga    60
accgctggag agcaactgca taaggctatg aagagatacg ccctggttcc tggaacaatt   120
gcttttacag atgcacatat cgaggtgaac atcacgtacg cggaatactt cgaaatgtcc   180
gttcggttgg cagaagctat gaaacgatat gggctgaata caaatcacag aatcgtcgta   240
tgcagtgaaa actctcttca attctttatg ccggtgttgg gcgcgttatt tatcggagtt   300
gcagttgcgc ccgcgaacga catttataat gaacgtgaat tgctcaacag tatgaacatt   360
tcgcagccta ccgtagtgtt tgtttccaaa aagggggttgc aaaaaattt gaacgtgcaa   420
aaaaaattac caataatcca gaaaattatt atcatggatt ctaaaacgga ttaccaggga   480
tttcagtcga tgtacacgtt cgtcacatct catctacctc ccggttttaa tgaatacgat   540
tttgtaccag agtcctttga tcgtgacaaa acaattgcac tgataatgaa ttcctctgga   600
tctactgggt tacctaaggg tgtggcccct ccgcatagaa ctgcctgcgt cagattctcg   660
catgccagag atcctatttt tggcaatcaa atcattccgg atactgcgat tttaagtgtt   720
gttccattcc atcacggttt tggaatgttt actacactcg atatttgat atgtggattt   780
cgagtcgtct taatgtatag atttgaagaa gagctgtttt tacgatccct tcaggattac   840
aaaattcaaa gtgcgttgct agtaccaacc ctatttcat tcttcgccaa aagcactctg   900
attgacaaat acgatttatc taatttacac gaaattgctt ctgggggcgc acctctttcg   960
aaagaagtcg gggaagcggt tgcaaaacgc ttccatcttc cagggatacg acaaggatat  1020
```

-continued

```
gggctcactg agactacatc agctattctg attacacccg aggggggatga taaaccgggc   1080 gcggtcggta agttgttcc atttttgaa gcgaaggttg tggatctgga taccgggaaa    1140
acgctgggcg ttaatcagag aggcgaatta tgtgtcagag gacctatgat tatgtccggt   1200
tatgtaaaca atccggaagc gaccaacgcc ttgattgaca aggatggatg gctacattct   1260
ggagacatag cttactggga cgaagacgaa cacttcttca tagttgaccg cttgaagtct   1320
ttaattaaat acaaaggata tcaggtggcc cccgctgaat tggaatcgat attgttacaa   1380 cacccccaaca tcttcgacgc gggcgtggca ggtcttcccg acgatgacgc cggtgaactt   1440
cccgccgccg ttgttgtttt ggagcacgga agacgatga cggaaaaaga gatcgtggat    1500
tacgtcgcca gtcaagtaac aaccgcgaaa aagttgcgcg gaggagttgt gtttgtggac   1560
gaagtaccga aaggtcttac cggaaaactc gacgcaagaa aaatcagaga gatcctcata   1620
aaggccaaga agggcggaaa gtccaaattg taa                                1653
```

<210> SEQ ID NO 3
<211> LENGTH: 550
<212> TYPE: PRT
<213> ORGANISM: Photinus pyralis

<400> SEQUENCE: 3

```
Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asn Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Asn Ile Ser Gln Pro Thr Val Val Phe Val
        115                 120                 125

Ser Lys Lys Gly Leu Gln Lys Ile Leu Asn Val Gln Lys Lys Leu Pro
    130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
        195                 200                 205

Ala Leu Pro His Arg Thr Ala Cys Val Arg Phe Ser His Ala Arg Asp
    210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255
```

```
Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
            275                 280                 285

Pro Thr Leu Phe Ser Phe Phe Ala Lys Ser Thr Leu Ile Asp Lys Tyr
            290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
            340                 345                 350

Pro Glu Gly Asp Asp Lys Pro Gly Ala Val Gly Lys Val Val Pro Phe
            355                 360                 365

Phe Glu Ala Lys Val Val Asp Leu Asp Thr Gly Lys Thr Leu Gly Val
            370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp Glu His Phe
            420                 425                 430

Phe Ile Val Asp Arg Leu Lys Ser Leu Ile Lys Tyr Lys Gly Tyr Gln
            435                 440                 445

Val Ala Pro Ala Glu Leu Glu Ser Ile Leu Leu Gln His Pro Asn Ile
            450                 455                 460

Phe Asp Ala Gly Val Ala Gly Leu Pro Asp Asp Ala Gly Glu Leu
465                 470                 475                 480

Pro Ala Ala Val Val Val Leu Glu His Gly Lys Thr Met Thr Glu Lys
                485                 490                 495

Glu Ile Val Asp Tyr Val Ala Ser Gln Val Thr Thr Ala Lys Lys Leu
            500                 505                 510

Arg Gly Gly Val Val Phe Val Asp Glu Val Pro Lys Gly Leu Thr Gly
            515                 520                 525

Lys Leu Asp Ala Arg Lys Ile Arg Glu Ile Leu Ile Lys Ala Lys Lys
            530                 535                 540

Gly Gly Lys Ser Lys Leu
545                 550

<210> SEQ ID NO 4
<211> LENGTH: 1741
<212> TYPE: DNA
<213> ORGANISM: Artificial Sequence
<220> FEATURE:
<223> OTHER INFORMATION: Synthetic luciferase nucleic acid

<400> SEQUENCE: 4
atggaggacg ccaagaacat caagaagggc cccgccccct tctacccct cgaggacggc      60 accgccggcg agcagctcca caaggccatg aagcgctacg ccctcgtccc cggcaccatc     120
gccttcgtag gtttcctcca gctctcgcct ccagcacccg aggcacatct cgggcatctt     180
cacaacaaca gacactgaca tctcattctc acagaccgac gcccacatcg aggtcaacat     240
cacctacgcc gagtacttcg agatgtccgt ccgcctcgcc gaggccatga agcgctacgg     300
cctcaacacc aaccaccgca tcgtcgtctg ctccgagaac tccctccagt tcttcatgcc     360
```

```
                                            -continued
cgtcctcggc gccctcttca tcggcgtcgc cgtcgccccc gccaacgaca tctacaacga      420
gcgcgagctc ctcaactcca tgaacatctc ccagcccacc gtcgtcttcg tctccaagaa      480
gggcctccag aagatcctca acgtccagaa gaagctcccc atcatccaga agatcatcat      540
catggactcc aagaccgact accagggctt ccagtccatg tacaccttcg tcacctccca      600 cctcccccc  ggcttcaacg agtacgactt cgtccccgag tccttcgacc gcgacaagac      660
catcgccctc atcatgaact cctccggctc caccggcctc cccaagggcg tcgccctccc      720
ccaccgcacc gcctgcgtcc gcttctccca cgcccgcgac cccatcttcg gcaaccagat      780 catcccgac  accgccatcc tctccgtcgt ccccttccac cacggcttcg gcatgttcac      840
caccctcggc tacctcatct gcggcttccg cgtcgtcctc atgtaccgct cgaggagga       900 gctcttcctc cgctccctcc aggactacaa gatccagtcc gccctcctcg tccccaccct      960
cttctccttc ttcgccaagt ccaccctcat cgacaagtac gacctctcca acctccacga     1020
gatcgcctcc ggcggcgccc cctctccaa  ggaggtcggc gaggccgtcg ccaagcgctt     1080
ccacctcccc ggcatccgcc agggctacgg cctcaccgag accacctccg ccatcctcat     1140
cacccccgag ggcgacgaca gcccggcgc  cgtcggcaag gtcgtcccct tcttcgaggc     1200
caaggtcgtc gacctcgaca ccggcaagac cctcggcgtc aaccagcgcg gcgagctctg     1260
cgtccgcggc cccatgatca tgtccggcta cgtcaacaac cccgaggcca ccaacgccct     1320
catcgacaag gacggctggc tccactccgg cgacatcgcc tactgggacg aggacgagca     1380
cttcttcatc gtcgaccgcc tcaagtccct catcaagtac aagggctacc aggtcgcccc     1440
cgccgagctc gagtccatcc tcctccagca ccccaacatc ttcgacgccg gcgtcgccgg     1500
cctccccgac gacgacgccg gcgagctccc cgccgccgtc gtcgtcctcg agcacggcaa     1560
gaccatgacc gagaaggaga tcgtcgacta cgtcgcctcc caggtcacca ccgccaagaa     1620
gctccgcggc ggcgtcgtct tcgtcgacga ggtccccaag ggcctcaccg gcaagctcga     1680
cgcccgcaag atccgcgaga tcctcatcaa ggccaagaag ggcggcaagt ccaagctctg     1740
a                                                                    1741

<210> SEQ ID NO 5
<211> LENGTH: 88
<212> TYPE: DNA
<213> ORGANISM: Neurospora crassa

<400> SEQUENCE: 5
gtaggtttcc tccagctctc gcctccagca cccgaggcac atctcgggca tcttcacaac       60
aacagacact gacatctcat tctcacag                                          88
```

| | ***************** ** *** *** ** | |

NUCLEIC ACID SEQUENCES ENCODING LUCIFERASE FOR EXPRESSION IN FILAMENTOUS FUNGI

This application claims the benefit of priority from U.S. Provisional Patent Application Ser. No. 60/614,874, filed Sep. 30, 2004, the content of which is incorporated herein by reference in its entirety.

This invention was made in the course of research sponsored by the National Institute of General Medical Sciences (Grant No. R37 GM34985) and the National Institute of Mental Health (Grant No. R01 MH44651). The U.S. government may have certain rights in this invention.

INTRODUCTION

Background of the Invention

Bioluminescence is the light produced in certain organisms as a result of luciferase-mediated oxidation reactions. The luciferase genes, e.g., the genes from luminous beetle and, in particular, the luciferase from *Photinus pyralis* (the common firefly of North America), are very useful luminescent reporter genes. See, e.g., Bronstein, et al. ((1994) *Cal. Biochem.* 219:19-181) for a review of luminescent reporter gene assays.

The gene encoding luciferase was cloned from *Photinus pyralis*, and demonstrated to produce active enzyme in *E. coli* (de Wet, et al. (1987) *Mol. Cell. Biol.* 7 :725). Firefly luciferase has become highly valuable as a genetic reporter due to the convenience, sensitivity and linear range of the luminescence assay. Luciferase is used in virtually every experimental biological system, including prokaryotic and eukaryotic cell culture, transgenic plants and animals, and cell-free expression systems.

Engineering of luciferases has been reported. Sung and Hang ((1998) *Photochem. Photobiol.* 68(5):749-53) disclose that the N-terminal amino acid sequences of the firefly luciferase are important for the stability of the enzyme. Branchini et al. ((1998) *Biochemistry* 37(44):15311-9) performed site-directed mutagenesis of $His^{245}$ in firefly luciferase. White et al. ((1996) *Biochem. J.* 319(Pt 2):343-50) showed an improvement in the thermostability of the North American firefly luciferase by saturation mutagenesis at residue 354. Kajiyama and Nakano ((1994) *Biosci. Biotechnol. Biochem.* 58(6):1170-1) constructed firefly luciferase mutants from *Luciola lateralis* in which Ala at position 217 was replaced by each of three hydrophobic amino acid residues (Ile, Leu, and Val). U.S. Pat. No. 5,401,629 describes assay methods and compositions useful for measuring the transduction of an intracellular signal. U.S. Pat. No. 5,670,356 teaches modified luciferase gene sequences with the peroxisomal translocation sequence removed to yield a cytoplasmic form of the enzyme interfering restriction sites and genetic regulatory sites from the gene removed, and improved codon usage for mammalian cells.

Despite its utility as a reporter, however, native luciferase is not necessarily optimized for the wide variety of host organisms, e.g., filamentous fungi, in which it can be used. The present invention meets this need in providing nucleic acid sequences encoding luciferase for high levels of expression in filamentous fungi.

SUMMARY OF THE INVENTION

The present invention relates to a variant nucleic acid molecule encoding a luciferase for expression in an organism with a bias for cytosine (C) or guanine (G) in the third position of the codon, wherein the nucleic acid molecule has a G and C content of at least 50%. In particular embodiments, the nucleic acid molecule further contains at least one intron. Vectors, host cells, and kits containing the variant nucleic acid molecule are also provided.

The present invention also relates to a method for enhancing the level of luciferase enzyme in an organism with a bias for C or G in the third position of the codon. The method involves introducing into the organism a nucleic acid molecule encoding a luciferase having a G and C content of at least 50% so that the level of luciferase enzyme produced in the organism is enhanced.

BRIEF DESCRIPTION OF THE DRAWINGS

FIG. 2A-2C is an alignment of native *Photinus* pyralis nucleic acid sequences encoding luciferase and optimized nucleic acid sequences encoding luciferase which provide high levels of luciferase expression in organisms with a bias for C or G in the third position of the codon. "*" denotes nucleotides which are identical between the coding sequences.

DETAILED DESCRIPTION OF THE INVENTION

Figure 1:
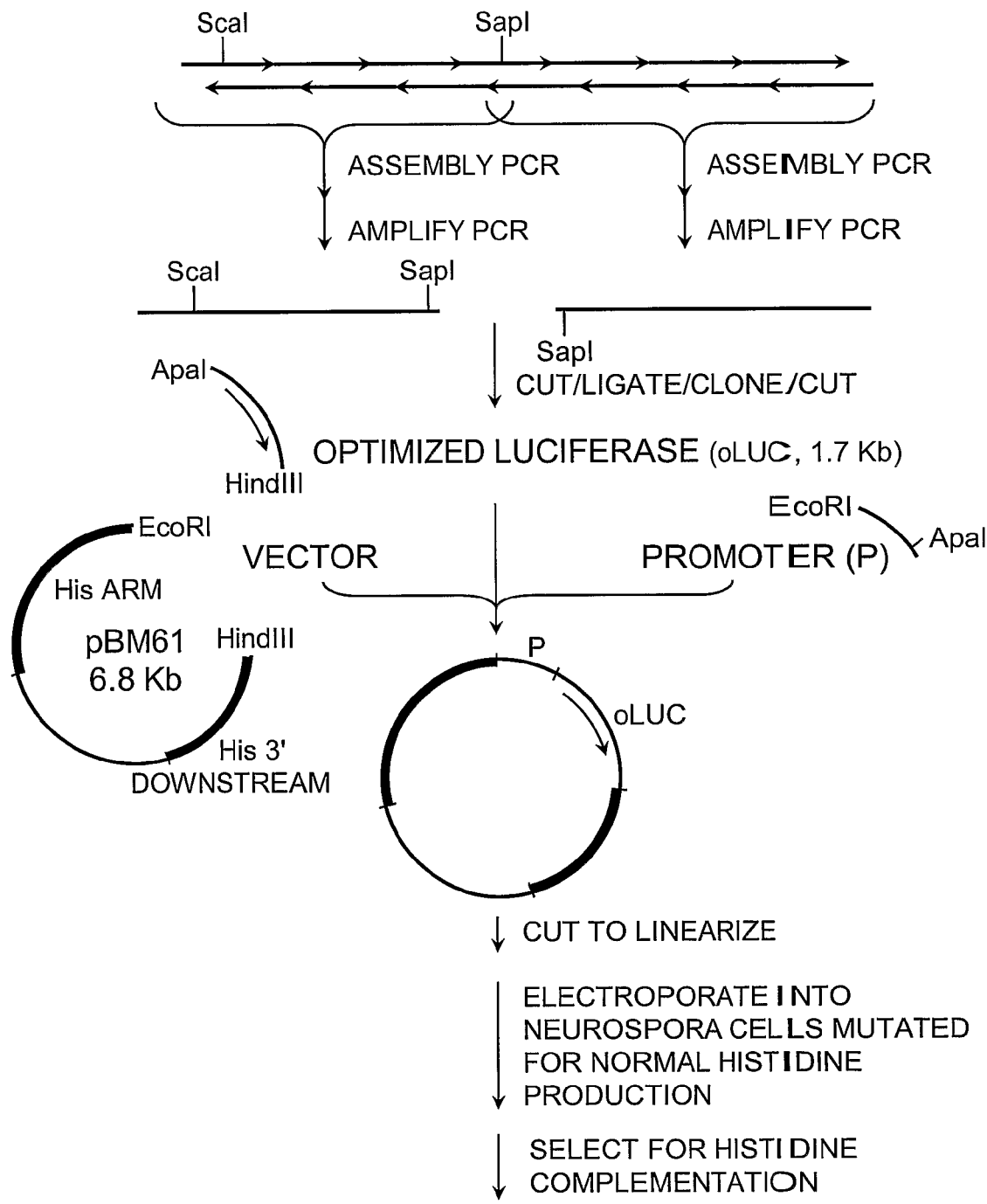
FIG. 1 illustrates the protocol for generating a novel G/C-rich nucleic acid molecule encoding luciferase which provides high levels of luciferase expression in organisms with a bias for cytosine (C) or guanine (G) in the third position of the codon.

A novel nucleic acid molecule encoding a luciferase enzyme has now been generated which has a higher level of in vivo expression in organisms with a bias for cytosine (C) or guanine (G) in the third position, and for some amino acids C in the first position, of the codon than has been achievable with native firefly luciferase reporter genes. This improved expression results in greater reliability and convenience as a genetic reporter in various microbial systems including filamentous fungi (e.g., *Neurospora, Aspergillus, Phytophthora*, etc.), Gram-positive bacteria (e.g., *Arthrobacter, Streptomyces, Mycobacterium, Pseudomonas* and the like), trypanosomes, and select vertebrates. Such applications include the detection, localization and measurement of filamentous fungi; measurement of protein expression, intracellular signaling and other turnover reactions in cells or fluids; DNA and RNA binding assays; and immunoassay and other protein assays.

To improve the general suitability of luciferase as a genetic reporter, a variant of the common *Photinus pyralis* luciferase gene has been developed. For reference, the nucleic acid and amino acid sequence of native *Photinus* pyralis luciferase is presented herein as SEQ ID NO:2 and SEQ ID NO:3, respectively. For the purposes of the present invention, the terms modified luciferase, variant luciferase, or optimized luciferase refer to a nucleic acid molecule encoding luciferase, wherein the nucleic acid molecule has been modified from its wild-type or native counterpart so that increased levels of expression in organisms with a bias for G or C in the third position of the codon is achieved. Desirably, the variant luciferase has a G+C content of at least 50%, 60% or more and encodes for a functional luciferase protein. In particular embodiments, the C content of the variant luciferase is in the range of about 30% to 50%, and most desirably about 40%. However, it should be understood that the modified, variant, or optimized luciferase encodes a protein with an amino acid sequence identical to functional wild-type luciferase (i.e.

SEQ ID NO:3) having an apparent molecular weight of 62 kilodaltons (kD) and emitting light in the presence of ATP, $Mg^{2+}$, molecular oxygen, and luciferin.

Codon usage generally refers to a bias toward preferred codons that generally correspond to the most abundant tRNA species (Kemura, et al., eds. (1992) In: *Transfer RNA in Protein Synthesis*, CRC, Boca Raton, Fla.). A positive correlation exists between codon usage bias and the level of gene expression (Gouy and Gautier (1982) *Nucleic Acids Res.* 10:7055-7074; Sharp and Li (1986) *J. Mol. Evol.* 24:28-38). This bias provides optimal translational efficiency, and is most pronounced in highly expressed genes in species whose effective population size is large (Bulmer (1991) *Genetics* 129:897-907; Li (1987) *J. Mol. Evol.* 24:337-345). As used in the context of the instant invention, an organism with a bias for G or C in the third position is intended to mean that of all the possible codons available for a particular amino acid, the organism efficiently translates mRNAs with amino acid codons having a G or C in the third position (i.e., Ala, Arg, Asn, Asp, Cys, Glu, Gln, Gly, His, Ile, Leu, Lys, Phe, Pro, Ser, Thr, Tyr and Val). As will be appreciated, a bias for G or C in the third position of the codon is generally accompanied by a bias for C in the first position (i.e., Arg and Leu). The inventive nucleic acid molecule was generated by making base substitutions in the native *Photinus pyralis* luciferase gene in accord with the codon usage bias for organisms with a bias for C or G in the third position of the codon, or more particularly a bias for C in the third position of the codon, to improve the expression level of luciferase in such organisms, without altering the amino acid sequence of the resulting enzyme. Using *Neurospora crassa* as an exemplary organism with a bias for C or G in the third position of the codon, the codon bias of native luciferase was modified based on the frequency of C or G in the first and third position of the codon of *Neurospora crassa* genes. Unlike *Photinus* pyralis which generally has a bias for adenine (A) or uracil (U), filamentous fungi generally have a propensity for cytosine C or guanine G (most notably C) in the third position of the codon and C in the first position, while codons containing A or U are less often used. (see Table 1).

TABLE 1

| Residue | Codon | N.c. | A.f. | P.i. | A.a. | M.g. | F.o. | P.p. |
|---|---|---|---|---|---|---|---|---|
| Arg | CGA | 7.0 | 9.4 | 3.4 | 8.8 | 8.2 | 13.0 | 6.4 |
|  | CGC | 17.7 | 15.4 | 16.0 | 11.7 | 18.9 | 13.7 | 4.3 |
|  | CGG | 8.5 | 10.8 | 1.8 | 5.8 | 8.5 | 3.9 | 2.1 |
|  | CGU | 8.9 | 11.1 | 13.8 | 10.0 | 8.9 | 9.0 | 4.3 |
|  | AGA | 7.9 | 7.6 | 1.6 | 7.0 | 5.7 | 7.0 | 17.0 |
|  | AGG | 11.8 | 6.0 | 1.6 | 6.2 | 10.8 | 3.8 | 0.0 |
| Leu | CUA | 5.9 | 6.6 | 5.7 | 9.4 | 5.3 | 5.8 | 8.5 |
|  | CUC | 26.9 | 23.2 | 18.9 | 25.5 | 25.9 | 27.4 | 9.6 |
|  | CUG | 18.2 | 24.5 | 33.5 | 15.7 | 24.7 | 13.6 | 14.9 |
|  | CUU | 14.2 | 15.8 | 10.2 | 19.5 | 13.5 | 20.8 | 15.2 |
|  | UUA | 2.7 | 4.2 | 1.1 | 3.8 | 2.8 | 3.4 | 21.6 |
|  | UUG | 14.9 | 15.8 | 9.2 | 12.4 | 13.2 | 9.6 | 22.3 |
| Ser | UCA | 9.2 | 10.2 | 4.9 | 11.4 | 10.0 | 9.8 | 3.5 |
|  | UCC | 20.1 | 18.2 | 11.7 | 17.7 | 15.2 | 13.4 | 11.3 |
|  | UCG | 14.5 | 14.9 | 26.6 | 12.1 | 18.2 | 6.4 | 7.8 |
|  | UCU | 12.0 | 13.8 | 7.3 | 18.3 | 11.0 | 18.3 | 16.7 |
|  | AGC | 17.4 | 15.7 | 16.3 | 15.5 | 19.3 | 15.2 | 3.5 |
|  | AGU | 8.6 | 9.6 | 6.0 | 6.8 | 6.2 | 7.9 | 12.0 |
| Thr | ACA | 10.7 | 12.0 | 8.5 | 14.0 | 10.6 | 12.0 | 17.7 |
|  | ACC | 24.9 | 20.6 | 27.8 | 22.2 | 23.5 | 23.8 | 13.5 |
|  | ACG | 13.6 | 11.9 | 30.9 | 11.1 | 15.1 | 7.3 | 10.6 |
|  | ACU | 11.2 | 14.0 | 13.1 | 15.4 | 10.5 | 18.2 | 12.8 |
| Pro | CCA | 12.3 | 11.4 | 7.9 | 10.5 | 11.4 | 11.9 | 13.1 |
|  | CCC | 22.5 | 17.4 | 15.4 | 14.1 | 18.5 | 18.2 | 12.0 |
|  | CCG | 14.5 | 12.6 | 20.8 | 10.4 | 15.3 | 5.8 | 12.0 |
|  | CCU | 15.1 | 16.6 | 12.8 | 14.4 | 11.5 | 23.4 | 15.9 |

TABLE 1-continued

| Residue | Codon | N.c. | A.f. | P.i. | A.a. | M.g. | F.o. | P.p. |
|---|---|---|---|---|---|---|---|---|
| Ala | GCA | 12.5 | 15.1 | 12.3 | 17.6 | 14.9 | 15.5 | 14.9 |
|  | GCC | 36.2 | 28.5 | 38.3 | 33.1 | 37.5 | 28.9 | 19.8 |
|  | GCG | 17.3 | 17.9 | 20.0 | 13.8 | 16.3 | 10.2 | 19.8 |
|  | GCU | 21.2 | 22.7 | 32.5 | 30.8 | 17.3 | 31.9 | 17.e7 |
| Gly | GGA | 13.6 | 14.4 | 10.9 | 16.5 | 13.0 | 15.5 | 31.5 |
|  | GGC | 29.2 | 25.1 | 37.8 | 25.6 | 34.0 | 26.9 | 18.8 |
|  | GGG | 10.9 | 10.2 | 3.4 | 8.0 | 9.4 | 4.4 | 16.3 |
|  | GGU | 18.4 | 19.1 | 24.0 | 21.2 | 16.9 | 24.2 | 17.7 |
| Val | GUA | 5.3 | 5.6 | 3.5 | 8.8 | 5.7 | 5.5 | 17.0 |
|  | GUC | 24.9 | 25.4 | 19.7 | 28.9 | 28.3 | 27.4 | 17.7 |
|  | GUG | 15.4 | 16.5 | 38.7 | 9.8 | 16.4 | 7.3 | 18.1 |
|  | GUU | 13.9 | 14.8 | 7.6 | 19.9 | 13.6 | 19.1 | 31.5 |
| Lys | AAA | 11.5 | 14.5 | 6.4 | 12.8 | 11.8 | 14.1 | 49.6 |
|  | AAG | 40.4 | 34.4 | 44.2 | 39.9 | 35.5 | 46.3 | 23.4 |
| Asn | AAC | 27.1 | 23.4 | 30.6 | 25.2 | 30.8 | 34.9 | 15.6 |
|  | AAU | 10.3 | 14.3 | 7.6 | 10.5 | 9.4 | 11.3 | 19.5 |
| Gln | CAA | 16.9 | 14.6 | 6.6 | 15.0 | 15.0 | 16.2 | 15.9 |
|  | CAG | 26.1 | 25.0 | 25.1 | 22.7 | 26.7 | 24.2 | 13.5 |
| His | CAC | 14.8 | 12.8 | 17.3 | 13.3 | 15.8 | 13.4 | 11.3 |
|  | CAU | 9.4 | 11.3 | 3.8 | 9.1 | 7.2 | 11.1 | 14.5 |
| Glu | GAA | 22.3 | 23.5 | 13.0 | 21.6 | 17.1 | 22.1 | 41.1 |
|  | GAG | 42.7 | 36.8 | 51.2 | 37.7 | 40.1 | 35.3 | 17.7 |
| Asp | GAC | 32.5 | 29.6 | 41.7 | 36.8 | 35.9 | 26.9 | 23.7 |
|  | GAU | 23.9 | 26.3 | 11.8 | 21.5 | 19.5 | 28.1 | 35.1 |
| Tyr | UAC | 17.4 | 18.1 | 30.8 | 17.5 | 20.7 | 23.5 | 17.7 |
|  | UAU | 8.4 | 11.5 | 5.6 | 8.6 | 7.3 | 11.4 | 17.0 |
| Cys | UGC | 7.7 | 7.7 | 11.3 | 12.1 | 9.8 | 8.6 | 2.8 |
|  | UGU | 3.3 | 4.7 | 4.6 | 7.1 | 3.4 | 5.5 | 3.9 |
| Phe | UUC | 22.2 | 26.1 | 28.7 | 26.3 | 23.5 | 26.6 | 19.8 |
|  | UUU | 11.7 | 13.1 | 6.8 | 11.6 | 14.4 | 10.5 | 30.1 |
| Ile | AUA | 4.0 | 4.6 | 1.2 | 8.8 | 6.1 | 3.5 | 16.3 |
|  | AUC | 26.6 | 27.9 | 27.0 | 27.0 | 28.7 | 29.7 | 16.7 |
|  | AUU | 14.0 | 17.4 | 13.0 | 15.6 | 15.3 | 17.0 | 33.7 |
| Met | AUG | 21.7 | 21.2 | 21.6 | 19.8 | 24.4 | 25.3 | 22.7 |
| Trp | UGG | 13.1 | 14.5 | 11.9 | 13.4 | 13.3 | 13.6 | 6.4 |
| Ter | UAA | 0.6 | 0.5 | 1.6 | 1.2 | 0.8 | 0.7 | 1.4 |
|  | UAG | 0.5 | 0.6 | 0.7 | 0.6 | 0.4 | 0.6 | 0.0 |
|  | UGA | 0.8 | 0.8 | 0.4 | 0.6 | 0.7 | 0.7 | 0.7 |

Numbers are presented as the frequency per thousand.
Data obtained from the codon page of kazusa.or.jp of the world-wide web.
N.c., *Neurospora crassa*;
A.f., *Aspergillus fumigatus*;
P.i., *Phytophthora infestans*;
A.a., *Alternaria alternata*;
M.g., *Magnaporthe grisea*;
F.o., *Fusarium oxysporum*;
P.p., *Photinus pyralis*.

The luciferase variant of the invention was generated using assembly PCR in accordance with standard methods, reagents, and PCR conditions (Stemmer, et al. (1995) *Gene* 164(1):49-53) using primers specific for the gene encoding native *Photinus pyralis* luciferase and a GC-Rich Taq such as FASTSTART™ Taq DNA Polymerase (Roche Molecular Biochemicals) or TAKARA LA TAQ™ (Takara Bio Inc.). See FIG. 1. As will be appreciated by the skilled artisan, however, any well-known method for altering genetic sequences can be used, e.g., oligonucleotide-mediated, site-specific mutagenesis directed against single-stranded plasmid templates (Lewis and Thompson (1990) *Nuc. Acids Res.* 18:3439-3443), and need not be further elaborated herein.

FIG. 2 shows the substitutions made (i.e., approximately 415 changes in 378 codons) in the native luciferase (540 codons) to generate the variant luciferase with optimized codon usage bias for improved expression in organisms with a bias for C or G in the third position of the codon. In general, the codons selected were as follows: Arg, CGC; Leu, CUC; Ser, UCC; Thr, ACC; Pro, CCC; Ala, GCC; Gly, GGC; Val, GUC; Lys, AAG; Asn, AAC; Gln, CAG; His, CAC; Glu, GAG; Asp, GAC; Tyr, UAC; Cys, UGC; Phe, UUC; and Ile, AUC. In cases where the first codon position could be C versus A or U (i.e., Arg and Leu), C was selected. Further, U was selected over A for the first codon position of Serine. The resulting overall base composition of the native versus variant luciferase is listed in Table 2.

TABLE 2

| Base | Native | | Variant | |
|---|---|---|---|---|
| | Occurrences | Percentage | Occurrences | Percentage |
| A | 479 | 29.0 | 313 | 18.9 |
| C | 346 | 20.9 | 705 | 42.6 |
| G | 394 | 23.8 | 372 | 22.5 |
| T | 434 | 26.3 | 263 | 15.9 |

As will be appreciated by one of skill in the art, all or a portion of the 387 codons modified as disclosed herein can be modified to create a variant luciferase. In other words, instead of the 415 codon modifications, a subset, e.g., 380 or 390 of the codon modifications, can be made to provide a variant luciferase with enhanced expression in an organism with a bias for C or G in the third position of the codon. In certain embodiments at least 60%, 65%, or 70%, (i.e., 324, 351, or 378 codons) of the wild-type 540 codons are modified to create a variant luciferase with enhanced expression in an organism with a bias for C or G in the third position of the codon. The nucleotide sequence of a variant luciferase with optimized expression in filamentous fungi is provided as SEQ ID NO:1.

To illustrate the utility of the inventive luciferase nucleic acid molecule, ccg-2 (GenBank accession no. (CAA47754.1) and frq (Aronson, et al. (1994) Science 263:1578-1584) promoters were independently cloned upstream of the variant luciferase nucleic acid molecule. The resulting fusions were inserted into suitable expression vectors and subsequently transformed into Neurospora crassa in accordance with standard methods. Unexpectedly, when the variant luciferase nucleic acid molecule were fused to the ccg-2 promoter, light emission from transformed cells could be detected with the naked eye in a darkened room. Transformed cells harboring the ccg-2- and frq-luciferase variant nucleic acid molecule were found to express levels of luciferase which were observable using either Roper or Hamamatsu cameras; a Roper camera has a 50× to 100× sensitivity, whereas a Hamamatsu camera has a 1× sensitivity. Under similar assay conditions, cells expressing native luciferase could not be visualized by available camera systems (standard scintillation counter, Turner luminometer, or Packard Top Count luminescence detector) and an N-terminally modified luciferase (Morgan, et al. (2003) *Fungal Genet. Biol.* 38(3):327-32) could be detected only when the strong ccg-2 promoter was used to drive luciferase and only when a Roper camera or similar camera was used.

Introduction of an intron into a gene has been found to enhance gene expression, stabilize the transcribed mRNA, as well as enhance the rate of mRNA export. To broaden the applicability and utility of the optimized luciferase, the first intron of the ccg-2 gene, a highly expressed *Neurospora crassa* transcript, was introduced into the nucleic acid molecule encoding the optimized luciferase in a position analogous to that of the intron found in the wild-type firefly gene first intron (i.e., at approximately nucleotide 127 of the coding sequence). The nucleic acid sequence encoding this intron containing transcript is provided herein as SEQ ID NO:4. The intron-containing, variant luciferase transcript was appropriately spliced by Neurospora, yielding a fully functional luciferase. Accordingly, in particular embodiments of the instant invention, a nucleic acid molecule encoding a variant luciferase further contains at least one intron. In certain embodiments, the intron is located at, or within 50 nucleotides, of the position of the intron in the wild-type firefly luciferase gene (i.e., position 127 of the coding sequence). Desirably, the intron is of a suitable length and contains suitable recognition sequences for efficient splicing in the organism being employed. The intron can be derived from the organism in which use is intended or can be from another organism so long as the organism in which use is intended can recognize and splice the intron from the coding sequence of the variant luciferase. It is also contemplated that at least two, three, or more introns can be introduced into the variant luciferase nucleic acid molecule of the instant invention. Intron and intron recognition sequences for genes of the organisms disclosed herein are well-known to those of skill in the art and can be readily identified using established gene prediction programs such as ORF Finder at NCBI, Gene Finder, Generation, GenScan, Glimmer, and the like available on the world-wide web. The nucleic acid sequence of an exemplary intron is disclosed herein as SEQ ID NO:5.

Assays employing the disclosed variant luciferase indicated that an increase in luciferin resulted in a corresponding increase in light emission. While, luciferin concentrations were not found to be saturating, it is contemplated that at very high levels, luciferin may become toxic. In addition, sprayed luciferin effectively generated light. Moreover, in this fungal system, the luciferin-luciferase reaction was strongly oxygen sensitive and luciferin was stable, lasting days to weeks.

Individual *Neurospora* hyphal cells expressing ccg-2-variant luciferase emitted light, and actively growing cells (e.g., those in the growth front of a race tube) and cells in high glucose growth conditions (e.g., 3.0% glucose) produced the most light. Further, high levels of variant luciferase expression were not found to be dependent on any particular strain or clone of *Neurospora*.

With regard to promoter-specific regulation of variant luciferase, the ccg-2 promoter revealed the following expression patterns: interband area darkening and conidial band areas brightened and left a lasting light in race tubes experiments; circadian behavior at the growth front disappeared under conditions where conidial bands do not form; and no rhythm-to-a slight rhythm was observed in lasting bands. frq promoter revealed the following expression patterns: strong peak-to-trough oscillations of a *Neurospora* colony can be seen on a sorbose plate, wherein the oscillation could persist for days; bands in a race tube continued to show light with no apparent diminishment in activity; and oscillatory activity was demonstrated in liquid media.

Accordingly, a variant luciferase as disclosed herein can enhance the level of luciferase produced in organisms (e.g., a filamentous fungus such as *Neurospora*) with a bias for C or G in the third position of the codon. As used herein, the level of luciferase is said to be enhanced when there is a 10- to 100-fold higher level of luciferase present in cells expressing the variant luciferase as compared to similar cells expressing a luciferase which has not been modified for expression in organisms with a bias for C or G in the third position of the codon (e.g., native luciferase, or a luciferase gene with modifications in the first 21 amino acids (Morgan, et al. (2003) supra)). In general, organisms in which the variant luciferase finds use include those organisms with a genomic G/C content of greater than 50%, 60%, 70% or more. Organisms, and host cells derived therefrom, generally having a bias for C or G in the third position of the codon, and typically also a bias for C in the first position, include, but are not limited to, filamentous fungi (e.g., Neurospora, Aspergillus, Phythoph-

*thora, Alternaria, Magnaporthe*, etc.), Gram-positive bacteria (e.g., *Arthrobacter, Streptomyces, Mycobacterium, Pseudomonas*, and the like), trypanosomes, and vertebrates such as chicken, bovine, and human, which have been shown to utilize either G or C at the third position of the codon (Marin, et al. (1989) *Nucl. Acid Res.* 17:6181-6189).

To further expand the utility of the luciferase encoded by the variant nucleic acid molecule disclosed herein, it is contemplated that additional modifications and changes can be made to the nucleic acid molecule while still retaining a luciferase enzyme having the desired characteristic of high levels of expression in organisms with a bias for C or G in the third position of the codon. For example, certain amino acids can be substituted for other amino acids in the protein structure without appreciable loss of bioluminescence. As will be appreciated by one of skill in the art, such changes create luciferase enzymes which are functionally equivalent (i.e., emit light in the presence of the appropriate substrates) but have altered protein thermostability (see, e.g., U.S. Pat. No. 6,265,177), enzyme efficiency, binding affinity of substrates (see, e.g., U.S. Pat. No. 6,265,177), or emission wavelength (see, e.g., U.S. Pat. Nos. 6,265,177; 6,495,355; and 5,330,906). So long as a mutation or change maintains the suitable codon bias of organisms with a bias for C or G in the third position of the codon, the resultant protein is considered functionally equivalent for the purposes of the invention. Accordingly, in particular embodiments, the nucleic acid molecule of the instant invention encodes a luciferase of SEQ ID NO:3 or a functional equivalent thereof.

The polypeptide sequence can be further modified, either chemically or by genetic engineering, to enable the luciferase to be targeted into a specific subcellular compartment. For example, a suitable sequence at the N-terminus will locate the bioluminescent protein in the mitochondria, while others will target the protein to the endoplasmic reticulum, optionally with a sequence at the C-terminus to retain it there. Genetically engineering the gene such that the protein contains a signal peptide can locate the protein to the inner or outer surface of the plasma membrane or within a particular intracellular organelle (e.g., peroxisome, mitochondrion, endoplasmic reticulum, golgi, secretory vesicle, nucleus or endosome).

The functional luciferase encoded by the inventive variant luciferase nucleic acid molecule is useful in a wide variety of assays including fusion proteins, gene expression studies (i.e., reporter gene) or screening purposes. Therefore, the present invention further relates to vectors and host cells expressing the variant luciferase nucleic acid molecule.

Insertion of the variant luciferase nucleic acid molecule into a vector can be carried out using standard molecular biology methods (e.g., PCR or restriction enzyme digestion and ligation). Advantageously, the modification of native luciferase nucleic acid molecule resulted in the elimination of AflIII, ApoI, ClaI, EcoRI, EcoRV, MluI, PacI, SphI, and XbaI from the native luciferase sequence. Therefore, these enzymes can be added to the repertoire of enzymes useful for cloning the variant luciferase nucleic acid molecule into vectors as disclosed herein.

As used herein, a vector includes a plasmid for amplifying, and not necessarily expressing, the luciferase variant nucleic acid molecule. Such vectors include, but are not limited to, pBluescript, pSP72, and pGEM vectors. A vector also includes an expression vector which is any type of genetic construct containing a luciferase variant nucleic acid molecule in which the nucleic acid molecule is capable of being transcribed and translated in a host cell. An expression vector of the invention should also direct translation into luciferase protein. Expression vectors will generally include restriction enzyme cleavage sites and other initial, terminal, and intermediate DNA sequences that are usually employed in vectors to facilitate their construction and use. Suitable expression vectors will be dependent on the host cell being transformed and are well-known to the skilled artisan.

Expression vectors for use in accordance with the present invention ordinarily include an origin of replication (as necessary), a selectable marker and a promoter operably linked to the gene(s) to be expressed. A polyadenylation site and transcriptional terminator sequences are desirably included on genes to be expressed in target cells. Ribosome binding sites, internal ribosome entry sites (IRES) and RNA splice sites can also be included. A vector can be integrated into the host cell chromosome or be maintained as an episome (e.g., in bacteria having a bias for G or C at the third position of the codon). Vectors will usually include an origin of replication functional in bacteria and a typical antibiotic resistance gene, allowing propagation and selection in transformed bacterial cells.

Specific initiation signals can also be included for efficient translation. These signals include the ATG initiation codon and adjacent sequences. Translational control signals within or outside of the luciferase coding sequence, including the ATG initiation codon, can additionally be provided in native or modified forms. One of ordinary skill in the art would readily be capable of determining this and providing the necessary signals. These exogenous translational control signals and initiation codons can be of a variety of origins, both natural and synthetic. The efficiency of expression is enhanced by the inclusion of appropriate transcription elements and transcription terminators. An appropriate polyadenylation site can also be included. Typically, the poly A addition site is placed about 30 to 2000 nucleotides downstream of the termination site of the protein at a position prior to transcription termination.

A number of selection systems can be used, including, but not limited to, the herpes simplex virus thymidine kinase (TK); hygromycin resistance; auxotrophic markers; antimetabolite resistance such as dihydrofolate reductase (dhfr) gene to confer resistance to methotrexate; neomycin resistance (bacterial in origin) for resistance to the aminoglycoside G-418; and the like.

Expression vectors will contain the variant luciferase nucleic acid molecule operably attached to a promoter. The promoter is generally positioned at the 5'-end of the transcription initiation site of the luciferase nucleic acids molecule such that the upstream promoter stimulates transcription of the DNA and promotes expression of the encoded luciferase protein. A promoter is operably attached when it is in the correct location and orientation in relation to the variant luciferase nucleic acid molecule to control RNA polymerase initiation and expression of the luciferase. The promoter used to express the variant luciferase is not critical to the present invention. The use of promoters is well-known in the art.

When a host cell or organism is used to replicate and/or express the luciferase from the nucleic acid molecule of the invention, the host cell or organism is within the scope of the invention. A host cell is a cell which is engineered or genetically modified with variant nucleic acid molecule of the present invention encoding the luciferase. The host cell can be isolated, in a tissue, in an organ, or in an organism. Alternatively, established cell lines that grow continuously in culture from a single cell or group of cells can be used in connection with the present invention A host cell can be transformed, transfected or transduced with a vector containing a variant luciferase nucleic acid molecule, e.g., by permeabilizing the cell membrane either chemically or physically or with viral- or *Agrobacterium*-mediated transfer. Calcium phosphate precipitation, DEAE-dextran, electroporation, and direct microinjection are examples of such methods. Alternatively, liposomes or protein conjugates formed with certain lipids and amphophilic peptides can be used for in vivo and in vitro transfection.

The variant luciferase nucleic acid molecule of the present invention can be used in a variety of assays as a reporter gene, e.g., to identify transformed cells; to measure gene expression in vitro, in vivo and ex vivo; to label specific microorganisms or cells of multicellular organisms; to label and locate fusion proteins; to study intracellular trafficking and the like. The variant luciferase nucleic acid molecule can be used in combination with other light emitting reporter genes, e.g., fluorescent proteins, luciferases that emit light at a different wavelength or convert substrates that emit light, change color and/or fluoresce, etc. Different colored reporter genes can be used simply to identify multiple cell populations in a mixed cell culture or to track multiple cell types, enabling differences in cell movement or migration to be visualized in real-time. Other embodiments include tracking and determining the location of cells or multiple proteins within a single cell, tissue or organism; differential promoter analyses in which gene expression from two different promoters is determined in the same cell, tissue or organism; imaging, and FACS sorting of mixed cell populations.

Using the variant luciferase nucleic acid molecule, a range of promoters can be tested for their suitability for use with a given gene, cell, or system, including in vitro uses (e.g., identifying a suitable promoter for use in recombinant expression, high level protein production, etc.) and in vivo uses (e.g. pre-clinical testing, gene therapy in subjects, etc).

For promoter analysis, the variant luciferase-coding sequence is operably linked to the promoter to be tested. Alternatively, the variant luciferase can be introduced, without a promoter, into the chromosome with the intent of identifying a previously uncharacterized promoter element (the technique referred to as promoter trapping). The production of light is related to the expression levels of the luciferase, which are controlled by the promoter element. The results are generally compared to a control gene, cell or system. Optimizing the combination of a given promoter and a given cell type in recombinant expression and protein production can often be necessary to ensure that the highest possible levels are achieved.

A further development of using promoters along with the variant luciferase nucleic acid molecule of the present invention is its use in screening protocols. In these embodiments, which are generally conducted in vitro, a genetically engineered cell is used to identify the presence of a particular compound or agent in a composition. The variant luciferase nucleic acid molecule is positioned downstream of a promoter that is known to be inducible by the agent that one wishes to identify. Expression of luciferase in the cells will normally be silent, and will be switched on by exposing the cell to a composition that contains the selected agent. In using a promoter that is responsive to, for example, a heavy metal, a toxin, a hormone, or other defined molecule, the presence of a heavy metal, toxin, cytokine or such like can readily be determined. Alternatively, constitutive expression of the reporter by genetically engineered cells can be useful in determining repressors of particular promoters.

Kits containing the variant luciferase nucleic acid molecule of the present invention are another embodiment of the present invention. Such kits will generally contain a variant luciferase nucleic acid molecule or a vector capable of expressing a variant luciferase nucleic acid molecule. The variant luciferase nucleic acid molecule or vector containing the same will be provided in a suitable formulation or as a lyophilized powder, and the kits can also contain, or be packaged with, one or more further molecular biological reagents, such as restriction enzymes, and with instructions for use.

What is claimed is:

1. An isolated nucleic acid molecule comprising the polynucleotide sequence of SEQ ID NO: 1 and encoding a *Photinus* luciferase of SEQ ID NO:3 for expression in an organism with a bias for cytosine (C) or guanine (G) in the third position of the codon, wherein the nucleic acid sequence has a G and C content of at least 50% and an intron comprising SEQ ID NO:5.

2. A vector comprising the nucleic acid molecule of claim 1.

3. An isolated host cell containing the vector of claim 2.

4. A method for enhancing the level of a luciferase enzyme in an organism with a bias for C or G in the third position of the codon comprising introducing into an organism with a bias for C or G in the third position of the codon a nucleic acid molecule of claim 1, thereby enhancing the level of luciferase enzyme produced in the organism.

5. A kit for expressing a luciferase enzyme in an organism with a bias for C or G in the third position of the codon comprising the nucleic acid molecule of claim 1.

6. An isolated nucleic acid molecule comprising SEQ ID NO:1.

7. The nucleic acid molecule of claim 6, further comprising an intron of SEQ ID NO:5.

* * * * *

UNITED STATES PATENT AND TRADEMARK OFFICE
CERTIFICATE OF CORRECTION

PATENT NO. : 7,666,616 B2  Page 1 of 1
APPLICATION NO. : 11/576168
DATED : February 23, 2010
INVENTOR(S) : Dunlap et al.

It is certified that error appears in the above-identified patent and that said Letters Patent is hereby corrected as shown below:

Column 17, in claim 1, line 58:

Please delete "sequence"
and please insert --molecule--.

Signed and Sealed this

Sixth Day of July, 2010

David J. Kappos
*Director of the United States Patent and Trademark Office*

UNITED STATES PATENT AND TRADEMARK OFFICE
CERTIFICATE OF CORRECTION

PATENT NO. : 7,666,616 B2  Page 1 of 1
APPLICATION NO. : 11/576168
DATED : February 23, 2010
INVENTOR(S) : Dunlap et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 230 days.

Signed and Sealed this

Twenty-eighth Day of December, 2010

David J. Kappos
*Director of the United States Patent and Trademark Office*